United States Patent [19]

Sauter et al.

[11] 4,350,518

[45] Sep. 21, 1982

[54] PLANT GROWTH REGULATING SUBSTITUTED ALKYLAMMONIUM SALTS

[75] Inventors: Hubert Sauter, Mannheim; Bernd Zeeh; Ernst Buschmann, both of Ludwigshafen; Johann Jung, Limburgerhof, all of Fed. Rep. of Germany

[73] Assignee: BASF Aktiengesellschaft, Fed. Rep. of Germany

[21] Appl. No.: 236,812

[22] Filed: Feb. 23, 1981

Related U.S. Application Data

[63] Continuation of Ser. No. 130,450, Mar. 14, 1980, abandoned.

[30] Foreign Application Priority Data

Apr. 4, 1979 [DE] Fed. Rep. of Germany ....... 2913523

[51] Int. Cl.³ .................. A01N 43/46; A01N 43/40; C07D 295/08
[52] U.S. Cl. ........................................ 71/88; 546/239; 546/330; 71/90; 546/334; 546/336; 71/92; 546/337; 546/339; 71/94; 546/340; 260/326.5 B; 71/95; 260/326.5 M; 260/326.5 S; 260/239 B; 260/326.5 SF; 260/239 BF; 260/326.25; 260/326.41; 260/326.62; 260/326.84; 544/58.1; 544/59; 544/158; 544/159; 544/160; 544/163; 544/165; 544/167; 544/174; 544/224; 544/133; 546/230; 546/232; 546/233; 546/234; 546/236; 546/237; 546/238
[58] Field of Search ............... 546/230, 232, 233, 234, 546/236, 237, 238, 239; 260/326.41, 326.5 M, 326.5 S, 326.5 SF, 326.62, 326.84, 239 B, 239 BF; 71/88, 95, 94

[56] References Cited

U.S. PATENT DOCUMENTS

| | | | |
|---|---|---|---|
| 3,142,554 | 7/1964 | Godfrey | 71/94 X |
| 3,255,196 | 6/1966 | Debarre et al. | 546/230 X |
| 3,275,629 | 9/1966 | Baizer | 71/94 X |
| 3,542,538 | 11/1970 | Jung et al. | 71/94 X |
| 3,564,046 | 2/1971 | Newhall | 71/94 X |
| 3,850,611 | 11/1974 | Nakanishi et al. | 71/94 X |

FOREIGN PATENT DOCUMENTS

| | | |
|---|---|---|
| 422758 | 4/1967 | Switzerland . |
| 952736 | 3/1964 | United Kingdom . |
| 982572 | 2/1965 | United Kingdom . |
| 1310372 | 3/1973 | United Kingdom . |

OTHER PUBLICATIONS

Shapilov, O., et al., *Zh. Prikl. Khim.*, 43(9), 2057–2060 (1970).

*Primary Examiner*—Richard A. Schwartz
*Attorney, Agent, or Firm*—Keil & Witherspoon

[57] ABSTRACT

Substituted alkylammonium salts of the formula

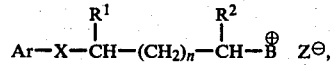

where Ar denotes substituted phenyl, X denotes oxygen or sulfur, n denotes one of the integers 0, 1 and 2, B denotes bicyclic quinuclidine, bicyclic pyrrolizidine or substituted ammonium, and Z denotes the anion of a nonphytotoxic acid, the manufacture of these compounds, and their use as plant growth regulators.

5 Claims, No Drawings

PLANT GROWTH REGULATING SUBSTITUTED ALKYLAMMONIUM SALTS

This is a continuation of application Ser. No. 130,450, filed Mar. 14, 1980. now abandoned.

The present invention relates to new, substituted alkylammonium salts, viz., certain aryloxy- und arylthioalkylammonium salts, agents for regulating plant growth containing these compounds, the use of these compounds and agents for regulating plant growth, and processes for manufacturing the new compounds.

A number of heterocyclic quaternary aryloxyalkylammonium salts having an antibacterial or pharmaceutical action have already been disclosed in the literature (e.g., British No. 952,736, British No. 863,197, German Laid-Open Application DE-OS No. 2,234,080 and Z. Prikl. Chim., 43, 2057, 1970). Further, a few of such compounds have also been suggested for technical uses, e.g., as leveling auxiliaries for the dyeing of polyacrylonitrile (German Laid-Open Application DE-OS No. 2,206,267). However, there is no reference in these publications to a plant-regulating action of such compounds. It has further been proposed to use certain quaternary phenoxyethylammonium salts (the quaternary nitrogen of which is, however, not part of a heterocycle) as agents for regulating plant growth (German Laid-Open Application DE-OS No. 2,017,497). Their action is, however, not always satisfactory, particularly at low application rates.

Quaternary ammonium compounds having a completely different structure have also been disclosed, e.g., 2-chloroethyltrimethylammonium chloride (CCC, U.S. Pat. No. 3,156,544). However, these compounds are not quaternary aryloxyalkylammonium or arylthioalkylammonium salts, and their action, particularly at low application rates, is not always satisfactory.

The present invention seeks to provide substituted alkylammonium salts of the formula

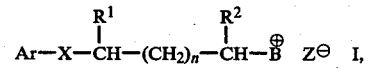

where Ar denotes phenyl substituted by trifluoromethyl, nitro, cyano, $C_2$-$C_4$-alkylcarbonyl or $C_2$-$C_4$-alkylcarbonylamino, or by 2 to 3 identical or different substituents selected from the group consisting of alkyl, alkenyl, alkynyl, cycloalkyl, alkoxy, alkenoyloxy, alkynoyloxy, alkylthio, haloalkyl, haloalkoxy, haloalkylthio, alkylcarbonylamino, alkylsulfonyl, alkylaminosulfonyl, dialkylaminosulfonyl, all of a maximum of 6 carbon atoms, fluoro, chloro, bromo, iodo, nitro, cyano, aminosulfonyl, phenyl and benzyl, X denotes oxygen or sulfur, n denotes one of the integers 0, 1 and 2, $R^1$ and $R^2$ are identical or different and each denotes hydrogen or $C_1$-$C_4$-alkyl, B denotes bicyclic quinuclidine, bicyclic pyrrolidizine or

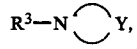

Y denoting a —$(CH_2)_4$—, —$(CH_2)_5$—, —$(CH_2)_6$—, —$(CH_2)_7$—, —$CH_2$13 CH=CH—$(CH_2)_2$—, —$(CH_2)_2$—O—$(CH_2)_2$—, $(CH_2)_2$—S—$(CH_2)_2$—, —NH—$(CH_2)_4$— or —NH—$CH_2$—CH=CH—$CH_2$— group which is unsubstituted or substituted by from 1 to 3 identical or different radicals selected from the group consisting of $C_1$-$C_4$-alkyl, $C_1$-$C_4$-alkoxy, $C_1$-$C_4$-haloalkyl, chloro, bromo, hydroxy and cyano, and $R^3$ denoting linear or branched $C_1$-$C_6$-alkyl, $C_2$-$C_6$-alkenyl or $C_2$-$C_6$-alkynyl, or benzyl, each of which is unsubstituted or substituted by halogen, hydroxy, cyano, $C_1$-$C_4$-alkoxy or $C_1$-$C_4$-alkylcarbonyl, and Z denotes the anion of any nonphytotoxic acid HX.

Examples of meanings for Ar are 3-trifluoromethylphenyl, 4-trifluoromethylphenyl, 2,4-dichlorophenyl, 3,4-dichlorophenyl, 3,5-dichlorophenyl, 2,6-dichlorophenyl, 2,4,5-trichlorophenyl, 2,4,6-trichlorophenyl, 2-chloro-4-fluorophenyl, 2-chloro-4-bromophenyl, 2-methyl-4-chlorophenyl, 2-chloro-4-phenylphenyl, 2-benzyl-4-chlorophenyl, 3,5-diethylphenyl, 2,4,6-trimethylphenyl, 2,6-dichloro-4-nitrophenyl, 2,6-diiodo-4-cyanophenyl, 2-methoxy-4-methylphenyl, 4-cyanophenyl, 3-nitrophenyl, 2-methyl-4-methylthiophenyl, 4-chloro-2-methylphenyl, 4-nitro-3-trifluoromethylphenyl, 2-chloro-4-nitrophenyl, 3,5-dimethoxyphenyl, and 3-acetylaminophenyl.

Preferred compounds are those in which X is oxygen, $R^1$ and $R^2$ are both hydrogen and n is 0.

In a further group of preferred compounds, B denotes bicyclic pyrrolidizine, or a pyrrolidine, piperidine, morpholine or hexamethylenimine ring substituted on the quaternary nitrogen by $R^3$.

Preferred radicals for $R^3$ are methyl, ethyl, propyl, butyl, allyl, propargyl, 2-chloroethyl, 2-bromoethyl, cyanomethyl, methylcarbonylmethyl, 2-chloropropen-3-yl, 2-methylpropen-3-yl and 2-buten-1-yl.

As the action of the compounds of the formula I according to the invention is attributable to the cation, any anion $Z^\ominus$ of a nonphytotoxic acid may be selected. $Z^\ominus$ denotes for instance acetate, methylsulfonate, p-toluenesulfonate, p-dodecylbenzenesulfonate, nitrate, phosphate, iodide, sulfate, methosulfate and particularly chloride or bromide. The anion $Z^\ominus$ is normally determined by the quaternization agent of the formula II or V which is selected; however, other anions $Z^\ominus$ may subsequently readily be introduced by ion exchange in accordance with generally known methods (e.g., Houben-Weyl, Methoden der Organischen Chemie, 11/2, 620-626 and 1/1, 544, Thieme-Verlag, Stuttgart, 1958).

The substituted alkylammonium salts of the formula I may be produced by (a) reacting a compound of the formula

where Ar, X, $R^1$, n and $R^2$ have the above meanings and Z denotes a nucleofugic leaving group, with a tertiary amine of the formula

B    III, where B has the above meanings, or (b) alkylating a compound of the formula

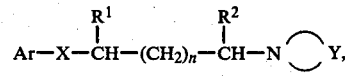

where Ar, X, $R^1$, n, $R^2$ and Y have the above meanings, with an alkylating agent of the formula $$R^3-Z \qquad \qquad V,$$

where $R^3$ has the above meanings and Z denotes a nucleofugic leaving group, to give a quaternary salt of the formula I.

Particularly suitable nucleofugic leaving groups for process (a) are chlorine, bromine, iodine, methylsulfonate and p-toluenesulfonate. Compounds II and III may be reacted in the presence or absence of a solvent or diluent, such as water or the conventional organic solvents, e.g., hydrocarbons, halohydrocarbons, ketones, alcohols, ethers, nitriles, esters and dimethylformamide, in homogeneous or nonhomogeneous phase and at from 20° to 150° C., preferably 50° to 120° C. Reactants II and III may be used in any ratio; it is, however, preferred to employ equimolar amounts or an excess of amine III.

The compounds of the formula II are generally known compounds or may readily be prepared by conventional processes, e.g., by monoalkylation of phenols ArOH or thiophenols ArSH with aliphatic dihalides such as 1,2-dibromoethane, 1,3-dibromopropane or 1,4-dibromobutane, preferably in water or, more preferably, in boiling diethylketone or cyclopentanone in the presence of at least equivalent amounts of potassium carbonate (cf. Houben-Weyl, Methoden der Organischen Chemie, 6/3, 54–59, Thieme-Verlag, Stuttgart, 1965, and Examples 1 and 3).

Examples of tertiary amines of the formula III which may be used are N-methylpyrrolidine, N-ethylpyrrolidine, N-allylpyrrolidine, N-propylpyrrolidine, N-butylpyrrolidine, N-methylpiperidine, N-methylhexamethylenimine, 2,4,6-trimethylmorpholine, quinuclidine and pyrrolizidine.

Examples of alkylating agents of the formula V which may be used for process (b) are methyl chloride, methyl bromide, methyl iodide, dimethyl sulfate, benzyl chloride, allyl bromide, propargyl chloride, isopentyl bromide, chloroacetone, chloroacetonitrile and 2-methoxyethyl tosylate. Alkylation is carried out without a diluent or solvent or in the presence of a diluent or solvent such as water, ethanol, acetone, acetonitrile, ethyl acetate, ether, toluene or dimethylformamide, in homogeneous or nonhomogeneous phase and at from 0° to 150° C., preferably 20° to 120° C. The ratio of the reactants to each other may be varied within wide limits; it is, however, preferred to use equimolar amounts or an up to 10-fold molar excess of the alkylating agent (cf. Houben-Weyl, Methoden der Organischen Chemie, 11/2, 591–601, Thieme-Verlag, Stuttgart, 1958, and Examples 2 and 4). Suitable nucleofugic leaving groups are the same as those given for process (a).

The tertiary amines of the formula IV are known compounds or are readily accessible by conventional methods, e.g., in accordance with the scheme

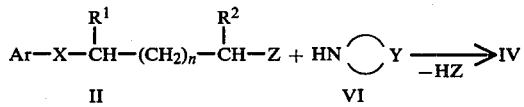

by alkylation of secondary amines of the formula VI, where Y has the above meanings, with the abovementioned compounds of the formula II. The reaction conditions are the same as those for the reaction II+III→I, it being preferred here to employ a 2- to 10-fold molar excess of the amine of the formula VI. The HX formed in the reaction may readily be removed, e.g., by treating the product mixture with aqueous alkali metal hydroxides, or by filtering off any acid addition salt

which may have precipitated (cf. Example 2).

A further conventional method for synthesizing tertiary amines of the formula IV is to react phenols or thiophenols of the formula VII, or alkali metals salts thereof, in which Ar and X have the above meanings, with tertiary amines of the formula VIII, or acid addition salts thereof, where $R^1$, n, $R^2$ and Y have the above meanings and Z denotes a nucleofugic leaving group, preferably chlorine, bromine, iodine, methanesulfonate or p-toluenesulfonate (cf. Houben-Weyl, Methoden der Organischen Chemie, 6/3, pp. 54–59, Thieme-Verlag, Stuttgart, 1965, and Example 4), in accordance with the scheme:

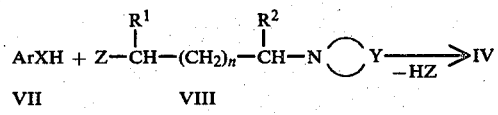

Examples of amines of the formula VIII which may be used are N-(2-chloroethyl)-pyrrolidine, N-(2-chloroethyl)-piperidine, N-(2-chloropropyl)-pyrrolidine and N-(2-chloroethyl)-hexamethylenimine.

For the synthesis of intermediates of formulae II and IV, for example the following phenols and thiophenols may be used: 2,4-dichlorophenol, 2,4-dichlorothiophenyl, 3,4-dichlorophenol, 3,4-dichlorothiophenyl, 3,5-dichlorophenol, 2,6-dichlorophenol, 2,4,5-trichlorophenol, 2,4,5-trichlorothiophenol, 2,4,6-trichlorophenol, 2,3,4-trichlorothiophenol, 2-chloro-4-fluorophenol, 2-fluoro-4-chlorophenol, 2,6-dichloro-4-fluorophenol, 2,4-dibromophenol, 2,4,6-tribromophenol, 2-bromo-4-chlorophenol, 4-bromo-2-chlorophenol, 4-bromo-2,6-dichlorophenol, 4-cyano-2,6-diiodophenol, 2-trifluoromethylphenol, 3-trifluoromethylphenol, 4-trifluoromethylphenol, 4-nitro-3-trifluoromethylphenol, 2,4-dimethylphenol, 3,4-dimethylphenol, 3,5-dimethylphenol, 2,4,6-trimethylphenol, 3,5-diethylphenol, 3,5-diisopropylphenol, 2-chloro-4-methylphenol, 4-chloro-2-methylphenol, 2,4-dimethylthiophenol, 3,4-dichloro-2,6-dimethylphenol, 2,4-dichloro-6-methylphenol, 4-chloro-3-methylphenol, 2,6-dimethyl-4-nitrophenol, 2,4-dimethyl-6-nitrophenol, 2-methyl-4-(methylthio)-phenol, 3-methyl-4-(methylthio)-phenol, 4-methyl-2-methoxyphenol, 2-benzyl-4-chlorophenol, 2-chloro-4-phenylphenol, 4-bromo-2-phenylphenol, 2-nitrophenol, 3-nitrophenol, 4-nitrophenol, 2,4-dinitrophenol, 2-chloro-4-nitrophenol, 4-chloro-2-nitrophenol, 2,6-dichloro-4-nitrophenol, 4-cyanophenol, 3-cyanophenol, 2-cyanophenol, 3-acetylaminophenol, 4-formylaminophenol, 4-acetylaminophenol, 2-acetylphenol, 3-acetylphenol, 3-butyrylphenol, and 4-acetylphenol.

The following examples illustrate the manufacture of the compounds of the formula I according to the invention, and the intermediates of formulae II and IV required for their manufacture.

EXAMPLE 1

(a) Manufacture of the starting material

A mixture of 162 g of 3-trifluoromethylphenol, 570 g of 1,2-dibromoethane, 500 ml of cyclopentanone and 166 g of anhydrous pulverized potassium carbonate is refluxed for 24 hours, with stirring. Cyclopentanone and excess dibromoethane are then distilled off under reduced pressure, and the residue is taken up in 500 ml of methylene chloride and 200 ml of 10% strength sodium hydroxide solution. After the aqueous phase has been separated off, the organic layer is washed three times, each time with 200 ml of 10% strength sodium hydroxide solution, and once with 150 ml of water, then dried over sodium sulfate and concentrated under reduced pressure. The oily residue (174 g) contains the 1-bromo-2-(3-trifluoromethylphenoxy)-ethane.

IR (film): 1590, 1490, 1444, 1325, 1291, 1280, 1165, 1120, 1094, 1062, 790, 780, 693 cm$^{-1}$.

(b) Manufacture of the end product 10 g of 1-bromo-2-(3-trifluoromethylphenoxy)-ethane and 20 g of pyrrolizidine are heated at 100° C. for 6 hours. After the mixture has cooled, 10 ml of acetone and 15 ml of ether are added. The oil which precipitates crystallizes completely at −15° C. There is isolated 8 g of white crystals of N-2-(3-trifluoromethylphenoxy)-ethyl-pyrrolizidinium bromide, which are washed with ether. Melting point: 55°–57° C.

EXAMPLE 2

(a) Manufacture of the starting material 54 g of 1-bromo-2-(3-trifluoromethylphenoxy)-ethane, 100 ml of toluene and 45 g of heptamethylenimine are refluxed for 24 hours. After the mixture has cooled, the precipitate is filtered off and the filtrate is extracted twice, each time with 100 ml of 10% strength aqueous sodium hydroxide solution, and then five times, each time with 100 ml of water, dried over sodium sulfate and concentrated under reduced pressure. The oily residue (46 g) contains the N-2-(3-trifluoromethylphenoxy)-ethylheptamethylenimine.

IR (film): 2910, 1582, 1482, 1440, 1320, 1230, 1157, 1116, 1056 cm$^{-1}$.

(b) Manufacture of the end product

A mixture of 9.0 g of N-2-(3-trifluoromethylphenoxy)-ethylheptamethylenimine and 18.0 g of allyl bromide is refluxed for 11 hours. The excess allyl bromide is stripped off under reduced pressure and the residue is taken up in 10 ml of acetone. At −15° C., 7.0 g of brownish crystals of N-allyl-N-2-(3-trifluoromethylphenoxy)-ethyl-heptamethyleniminium bromide precipitate out from this solution and are washed with ethyl acetate. Melting point: 119°–125° C.

EXAMPLE 3

(a) Manufacture of the starting material

A mixture of 8.0 g of sodium hydroxide in 80 ml of water, 32 g of 2,4,6-trimethylphenol and 215 g of 1,4-dibromobutane is refluxed for 100 hours, with stirring. After the mixture has cooled, the aqueous phase is separated and the organic phase is extracted with 200 ml of methylene chloride. The combined organic phases are then extracted ten times, each time with 150 ml of water, dried over sodium sulfate, and freed from methylene chloride by concentration under reduced pressure. The residue is distilled under reduced pressure; after first runnings consisting of excess 1,4-dibromobutane, 24 g of 1-bromo-4-(2,4,6-trimethylphenoxy)-butane distil over at 110°–130° C./2–4 mm.

IR (film): 2910, 2860, 1483, 1442, 1374, 1308, 1245, 1216, 1147, 1039, 854 cm$^{-1}$.

(b) Manufacture of the end product

A mixture of 7.0 g of 1-bromo-4-(2,4,6-trimethylphenoxy)-butane and 20 g of N-methylpiperidine is refluxed for 8 hours. After the mixture has been cooled to 60° C., it is stirred with 20 ml of acetone; upon further cooling, a crystalline mash separates out which is filtered, after the addition of 20 ml of ether, and washed with toluene and acetone. There is obtained 8.0 g of pale yellow crystals of N-methyl-N-4-(2,4,6-trimethylphenoxy)-butylpiperidinium bromide. Melting point: 171°–173° C.

EXAMPLE 4

(a) Manufacture of the starting material

Under a nitrogen blanket and while stirring, a solution of 85 g of N-(2-chloroethyl)-pyrrolidinium hydrochloride is dripped into a solution of 100 g of sodium hydroxide and 160 g of 2,4,5-trichlorothiophenol in 2,400 ml of water. The resultant mixture is refluxed for 8 hours. After cooling, the precipitate is filtered, taken up in 1,000 ml of methylene chloride and washed twice, each time with 200 ml of 10% strength aqueous sodium hydroxide solution and once with 200 ml of water. After the organic phase has been dried over sodium sulfate and the methylene chloride distilled off under reduced pressure, there is obtained 147 g of N-2-(2,4,5-trichlorophenylthio)-ethyl-pyrrolidine. Melting point: 72°–74° C.

(b) Manufacture of the end product

A mixture of 15.5 g of N-2-(2,4,5-trichlorophenylthio)-ethyl-pyrrolidine, 12.5 g of 2-bromoethanol and 20 ml of acetonitrile is refluxed for 14 hours. After the mixture has cooled, 100 ml of ether is added. The precipitate which forms is filtered and washed with ether. There is obtained 18.3 g of crystals of N-2-hydroxyethyl-N-2-(2,4,5-trichlorophenylthio)-ethyl-pyrrolidinium bromide. Melting point: 135°–137° C.

The following compounds are further examples of compounds of the formula I according to the invention; the structures of most of them were confirmed by $^1$H nuclear resonance and infrared spectra:

5.

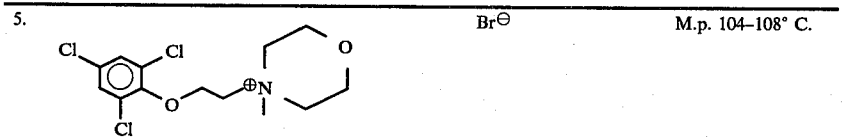

M.p. 104–108° C.

-continued
| | | | |
|---|---|---|---|
| 6. | 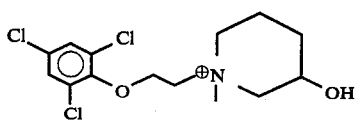 | Br⊖ | M.p. 140–143° C. |
| 7. | 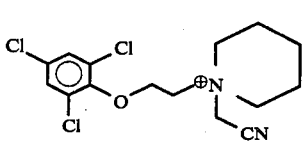 | Cl⊖ | M.p. 121–125° C. |
| 8. | 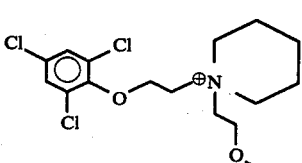 | ⊖O₃S—⟨⟩—CH₃ | M.p. 88–89° C. |
| 9. | 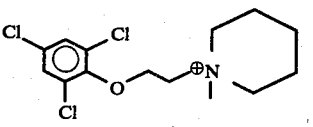 | ⊖O₃SOCH₃ | M.p. 135–142° C. |
| 10. | 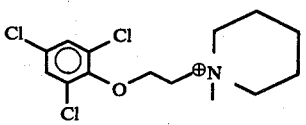 | Br⊖ | M.p. 198–200° C. |
| 11. | 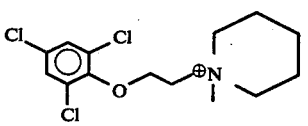 | I⊖ | M.p. 136–139° C. |
| 12. | 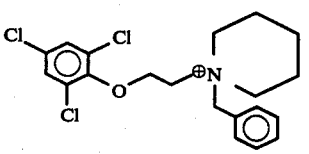 | Cl⊖ | M.p. 145–148° C. |
| 13. | 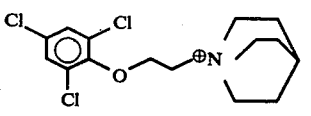 | Br⊖ | M.p. 178–180° C. |
| 14. | 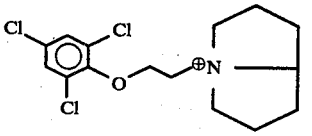 | Br⊖ | M.p. 141–144° C. |
| 15. | 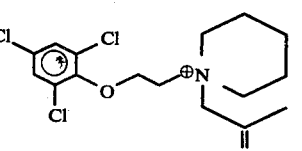 | Cl⊖ | M.p. 75–77° C. |

-continued
| | | | |
|---|---|---|---|
| 16. | 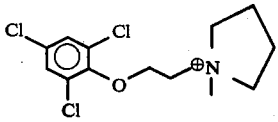 | Br⊖ | M.p. 62–65° C. |
| 17. | 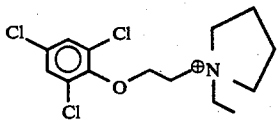 | Br⊖ | M.p. 116–118° C. |
| 18. | 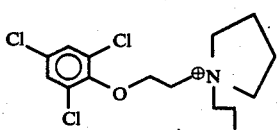 | Br⊖ | M.p. 177–178° C. |
| 19. | 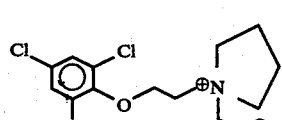 | Br⊖ | M.p. 165–168° C. |
| 20. | 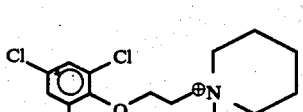 | Br⊖ | M.p. 150–152° C. |
| 21. | 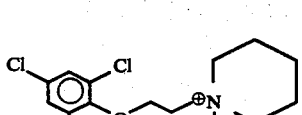 | Br⊖ | M.p. 183–184° C. |
| 22. | 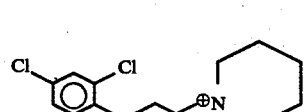 | Br⊖ | M.p. 155–156° C. |
| 23. | 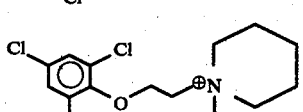 | Br⊖ | M.p. 184–187° C. |
| 24. | 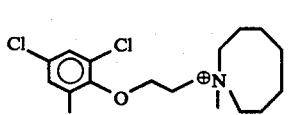 | Br⊖ | M.p. >200° C. |
| 25. | 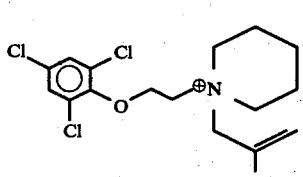 | Cl⊖ | M.p. 176–177° C. |
| 26. | 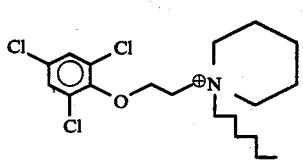 | Br⊖ | |

-continued
| | | | |
|---|---|---|---|
| 27. | 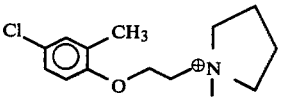 | Br⊖ | M.p. 58–61° C. |
| 28. | 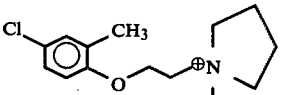 | Br⊖ | M.p. 165–167° C. |
| 29. | 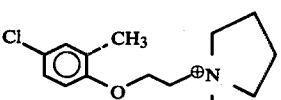 | Br⊖ | M.p. 104–107° C. |
| 30. | 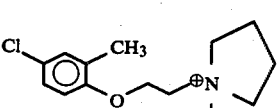 | Br⊖ | M.p. 101–103° C. |
| 31. | 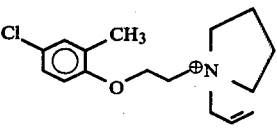 | Br⊖ | M.p. 138–139° C. |
| 32. | 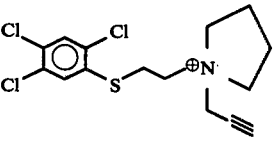 | Br⊖ | M.p. 106–109° C. |
| 33. | 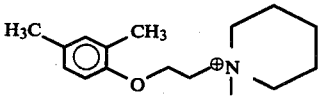 | Br⊖ | M.p. 145–147° C. |
| 34. | 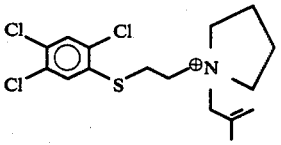 | Cl⊖ | M.p. 83–87° C. |
| 35. | 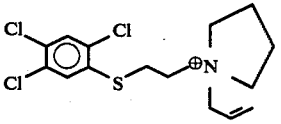 | Cl⊖ | M.p. 55–58° C. |
| 36. | 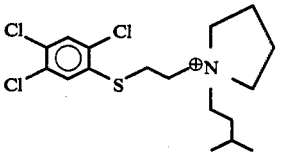 | Br⊖ | M.p. 130–133° C. |

-continued

| # | Structure | Anion | M.p. |
|---|---|---|---|
| 37. | 3-CF₃-C₆H₄-O-CH₂CH₂-N⁺(CH₃)(azepane) | Br⁻ | M.p. 179–181° C. |
| 38. | 3-CF₃-C₆H₄-O-CH₂CH₂CH₂-N⁺(CH₃)(piperidine) | Br⁻ | M.p. 156–157° C. |
| 39. | 3-CF₃-C₆H₄-O-CH₂CH₂-N⁺(C≡CH)(azocane) | Br⁻ | |
| 40. | 4-CF₃-C₆H₄-O-CH₂CH₂-N⁺(CH₃)(piperidine) | Br⁻ | M.p. 83–87° C. |
| 41. | 3-CF₃-C₆H₄-O-CH₂CH₂-N⁺(C₂H₅)(piperidine) | Br⁻ | M.p. 110–112° C. |
| 42. | 3-CF₃-C₆H₄-O-CH₂CH₂-N⁺(n-C₃H₇)(pyrrolidine) | Br⁻ | M.p. 137–139° C. |
| 43. | 3-CF₃-C₆H₄-O-(CH₂)₄-N⁺(n-C₄H₉)(pyrrolidine) | Br⁻ | M.p. 83–85° C. |
| 44. | 3-CF₃-C₆H₄-O-CH₂CH₂-N⁺(quinuclidine) | Br⁻ | M.p. 168–170° C. |
| 45. | 2,4-Cl₂-C₆H₃-O-CH₂CH₂-N⁺(CH₃)(azepane) | Br⁻ | M.p. 140–143° C. |
| 46. | 2,4-Cl₂-C₆H₃-O-CH₂CH₂-N⁺(CH₃)(piperidine) | Br⁻ | M.p. 181–182° C. |
| 47. | 2,4-Cl₂-C₆H₃-O-CH₂CH₂-N⁺(CH₃)(2,6-dimethylmorpholine) | Br⁻ | M.p. 204–209° C. (cis-trans mixture) |
| 48. | 2,4-Cl₂-C₆H₃-O-CH₂CH₂-N⁺(1,2,3,6-tetrahydropyridine) | Br⁻ | M.p. 131–134° C. |

-continued
| | | | |
|---|---|---|---|
| 49. | 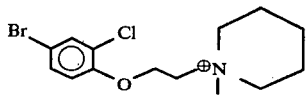 | Br⊖ | M.p. 200–202° C. |
| 50. | 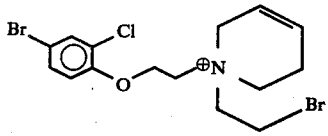 | Br⊖ | M.p. 155–159° C. |
| 51. | 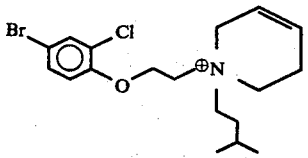 | Br⊖ | M.p. 139–143° C. |
| 52. | 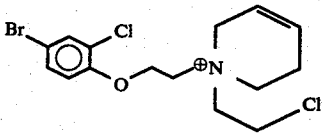 | Br⊖ | M.p. 141–144° C. |
| 53. | 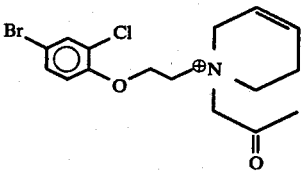 | Cl⊖ | M.p. 188–189° C. |
| 54. | 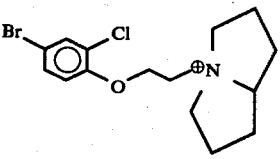 | Br⊖ | M.p. 91–93° C. |
| 55. | 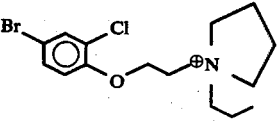 | Br⊖ | M.p. 153–154° C. |
| 56. | 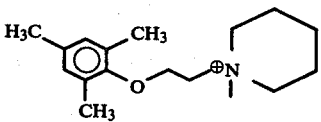 | Br⊖ | M.p. 193–195° C. |
| 57. | 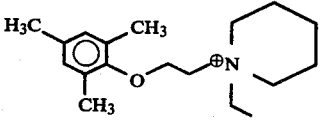 | Br⊖ | M.p. 176–178° C. |
| 58. | 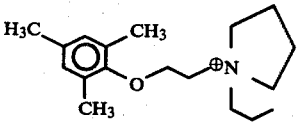 | Br⊖ | M.p. 187–188° C. |

-continued
| | | | |
|---|---|---|---|
| 59. | 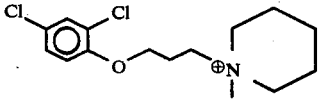 | Br⊖ | M.p. 148–151° C. |
| 60. | 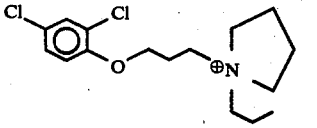 | Br⊖ | M.p. 122–127° C. |
| 61. | 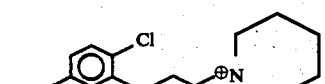 | Br⊖ | M.p. 144–148° C. |
| 62. | 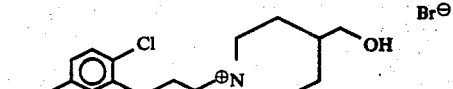 | Br⊖ | M.p. 160–161° C. |
| 63. | 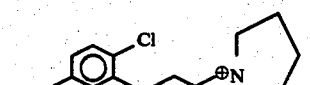 | Br⊖ | M.p. 146–148° C. |
| 64. | 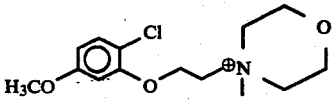 | Br⊖ | M.p. 162–165° C. (cis-trans mixture) |
| 65. | 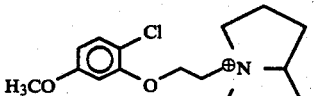 | Br⊖ | M.p. 125–126° C. |
| 66. | 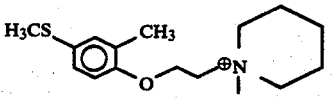 | Br⊖ | M.p. 69–73° C. |
| 67. | 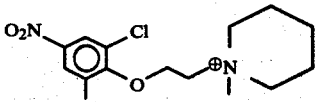 | Br⊖ | M.p. 163–165° C. |
| 68. | 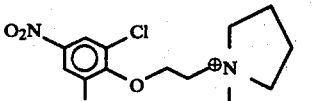 | Br⊖ | M.p. 62–66° C. |
| 69. | 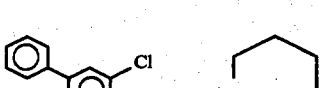 | Br⊖ | M.p. 158–161° C. |

-continued

| | | | |
|---|---|---|---|
| 70. | [3-chloro-biphenyl-O-CH2CH2-N+(CH3)-pyrrolidine] | Br⁻ | M.p. 152–156° C. |
| 71. | [3-chloro-biphenyl-O-CH2CH2-N+(propyl)-pyrrolidine] | Br⁻ | |
| 72. | [4-chloro-2-benzyl-phenyl-O-CH2CH2-N+(CH3)-piperidine] | Br⁻ | M.p. 145–147° C. |
| 73. | [4-chloro-2-benzyl-phenyl-O-CH2CH2-N+(CH3)-thiomorpholine] | Br⁻ | M.p. 183–186° C. |
| 74. | [4-chloro-2-benzyl-phenyl-O-CH2CH2-N+(methallyl)-thiomorpholine] | Cl⁻ | |
| 75. | [4-fluoro-2-chloro-phenyl-O-CH2CH2-N+(CH3)-piperidine] | Br⁻ | M.p. 157–162° C. |
| 76. | [4-fluoro-2-chloro-phenyl-O-CH2CH2-N+(CH2CH2CN)-piperidine] | Br⁻ | IR (film): 2940, 2238,1586,1484, 1252,1183,1050, 900,878,851,800, 752 cm⁻¹ |
| 77. | [4-cyano-2,6-diiodo-phenyl-O-CH2CH2-N+(CH3)-piperidine] | Br⁻ | M.p. 176–180° C. |
| 78. | [4-cyano-2,6-diiodo-phenyl-O-CH2CH2-N+(C2H5)-pyrrolidine] | Br⁻ | M.p. 164–170° C. |
| 79. | [4-cyano-2,6-diiodo-phenyl-O-CH2CH2-N+(CH3)-pyrrolidine] | Br⁻ | |

-continued
| | | | |
|---|---|---|---|
| 80. | 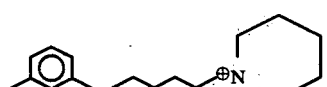 | Br⊖ | |
| 81. | 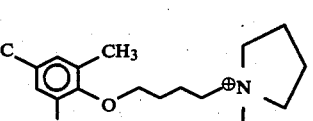 | Br⊖ | M.p. 123–125° C. |
| 82. | 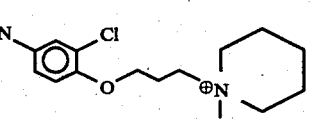 | Br⊖ | M.p. 160–163° C. |
| 83. | 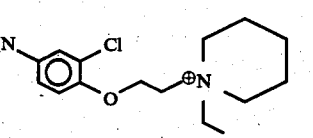 | Br⊖ | M.p. 109–113° C. |
| 84. | 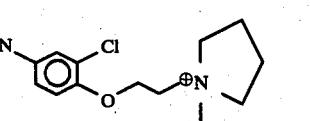 | Br⊖ | M.p. 170–174° C. |
| 85. | 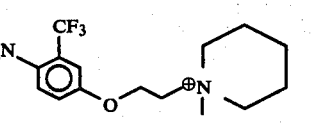 | Br⊖ | M.p. 165–170° C. |
| 86. | 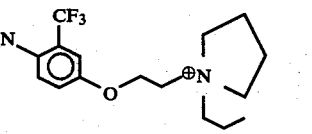 | Br⊖ | M.p. 179–180° C. |
| 87. | 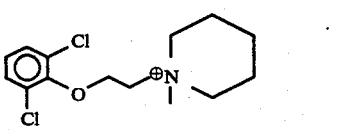 | Br⊖ | M.p. 121–123° C. |
| 88. | 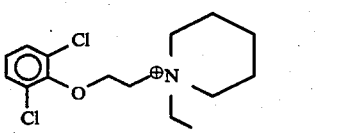 | Br⊖ | M.p. >200° C. |
| 89. | 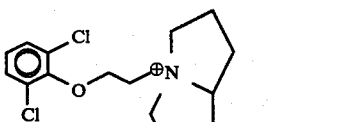 | Br⊖ | M.p. 79–80° C. |
| 90. | | Br⊖ | M.p. 50–56° C. |

-continued
| | | | |
|---|---|---|---|
| 91. | 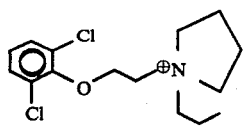 | Br⊖ | M.p. 219–220° C. |
| 92. | 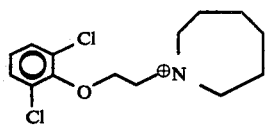 | Br⊖ | M.p. >200° C. |
| 93. | 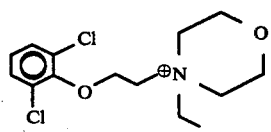 | Br⊖ | resin |
| 94. | 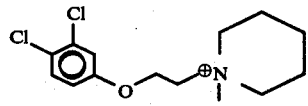 | Br⊖ | M.p. 146–149° C. |
| 95. | 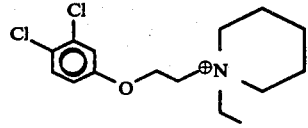 | Br⊖ | M.p. 136–139° C. |
| 96. | 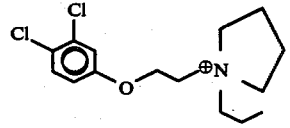 | Br⊖ | M.p. 139–142° C. |
| 97. | 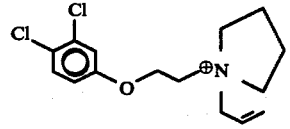 | Br⊖ | M.p. 173–177° C. |
| 98. | 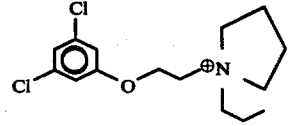 | Br⊖ | M.p. 115–117° C. |
| 99. | 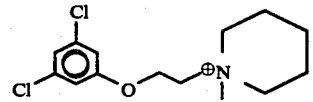 | Br⊖ | M.p. 166–168° C. |
| 100. | 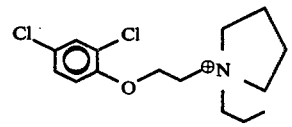 | Br⊖ | M.p. 144–145° C. |
| 101. | 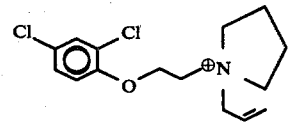 | Br⊖ | M.p. 142–143° C. |

-continued

| # | Structure | Anion | M.p. |
|---|---|---|---|
| 102. | 2,4-dimethylphenyl-O-CH₂CH₂-N⁺(pyrrolidine with propyl) | Br⁻ | M.p. 120–125° C. |
| 103. | 2,4,5-trichlorophenyl-S-CH₂CH₂-N⁺(Me)(pyrrolidine) | Br⁻ | M.p. 80–81° C. |
| 104. | 4-cyanophenyl-O-CH₂CH₂-N⁺(Me)(piperidine) | Br⁻ | M.p. 82–85° C. |
| 105. | 4-cyanophenyl-O-CH₂CH₂-N⁺(propyl)(pyrrolidine) | Br⁻ | M.p. 98–103° C. |
| 106. | 3-acetamidophenyl-O-CH₂CH₂-N⁺(Me)(piperidine) | Br⁻ | M.p. 174–178° C. |
| 107. | 3-acetamidophenyl-O-CH₂CH₂-N⁺(indolizidine) | Br⁻ | resin |
| 108 | 3-trifluoromethylphenyl-O-CH₂CH₂CH₂-N⁺(pyrrolidine with propyl) | Br⁻ | M.p. 103° C. |
| 109 | 4-methylthio-2-methylphenyl-O-CH₂CH₂-N⁺(pyrrolidine with propyl) | Br⁻ | M.p. 85–100° C. |
| 110 | 3-acetamidophenyl-O-CH₂CH₂-N⁺(pyrrolidine with propyl) | Br⁻ | resin |
| 111 | 3,4-dichlorophenyl-O-CH₂CH₂-N⁺(pyrrolidine)(CH₂-C(Cl)=CH₂) | Cl⁻ | M.p. 126–130° C. |

-continued
| | | | |
|---|---|---|---|
| 112 | 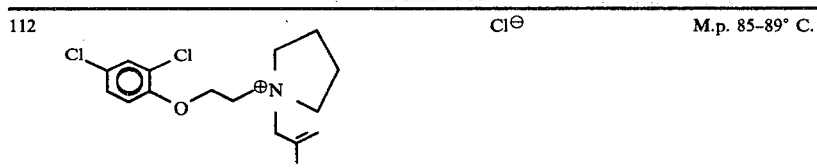 | Cl⊖ | M.p. 85–89° C. |
| 113 |  | Br⊖ | M.p. 166–168° C. |
| 114 |  | Br⊖ | M.p. 149–155° C. |
| 115 | 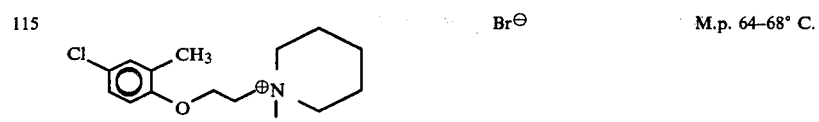 | Br⊖ | M.p. 64–68° C. |
| 116 | 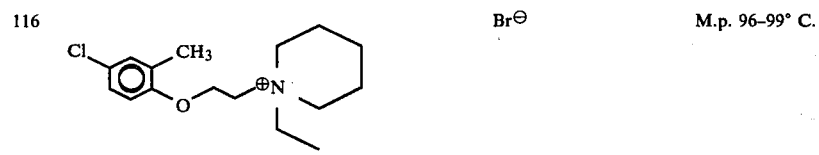 | Br⊖ | M.p. 96–99° C. |
| 117 | 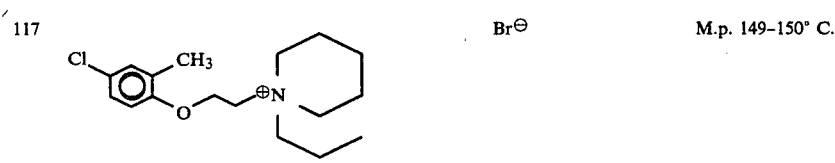 | Br⊖ | M.p. 149–150° C. |
| 118 |  | Br⊖ | M.p. 124–127° C. |
| 119 | 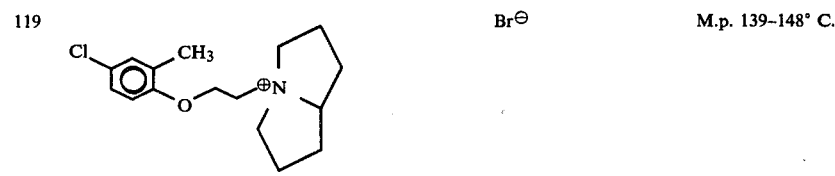 | Br⊖ | M.p. 139–148° C. |
| 120 | 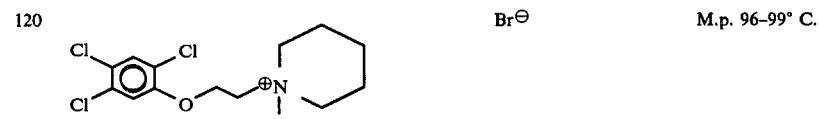 | Br⊖ | M.p. 96–99° C. |
| 121 |  | Br⊖ | M.p. 160–164° C. |
| 122 | 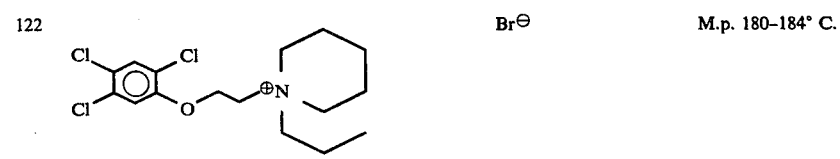 | Br⊖ | M.p. 180–184° C. |

| | | | |
|---|---|---|---|
| 123 | 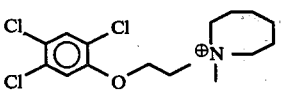 | Br⊖ | M.p. 90–92° C. |
| 124 | 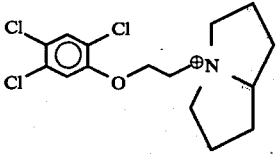 | Br⊖ | M.p. 159–160° C. |
| 125 | 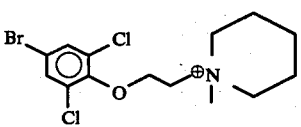 | Br⊖ | M.p. 225–227° C. |
| 126 | 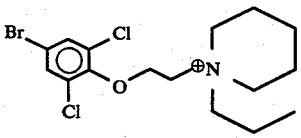 | Br⊖ | M.p. 180–184° C. |
| 127 | 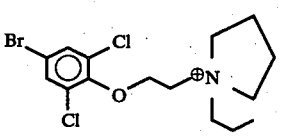 | Br⊖ | M.p. 181–184° C. |
| 128 | 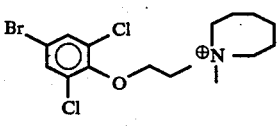 | Br⊖ | M.p. >230° C. |
| 129 | 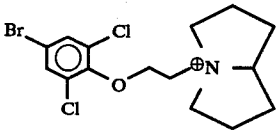 | Br⊖ | M.p. 90–92° C. |
| 130 | 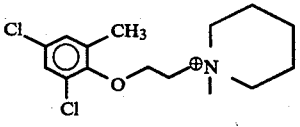 | Br⊖ | M.p. 193–197° C. |
| 131 | 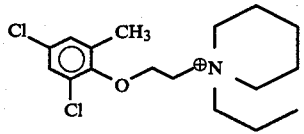 | Br⊖ | M.p. 141–147° C. |
| 132 | 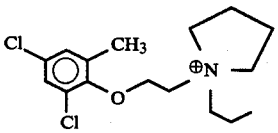 | Br⊖ | M.p. 69–73° C. |

-continued
| | | | |
|---|---|---|---|
| 133 | 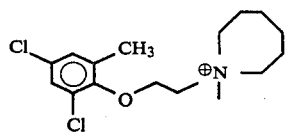 | Br⊖ | M.p. 225–227° C. |
| 134 | 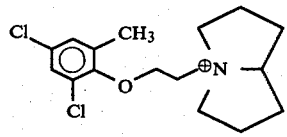 | Br⊖ | M.p. 90–95° C. |
| 135 | 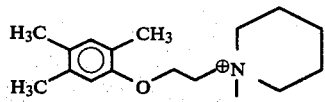 | Br⊖ | M.p. 152–155° C. |
| 136 | 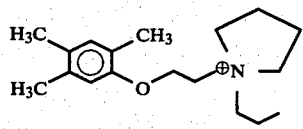 | Br⊖ | M.p. 182–184° C. |
| 137 | 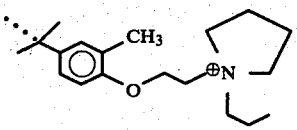 | Br⊖ | |
| 138 | 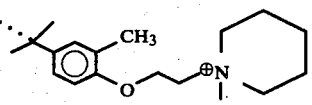 | Br⊖ | |
| 139 | 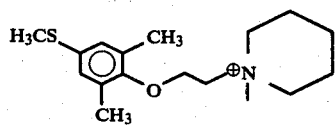 | Br⊖ | |
| 140 | 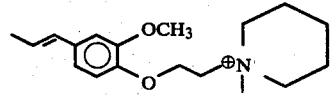 | Br⊖ | |
| 141 | 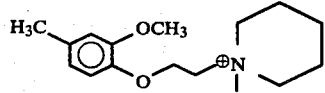 | Br⊖ | |
| 142 | 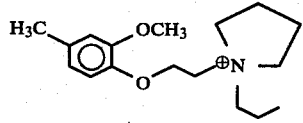 | Br⊖ | |
| 143 | 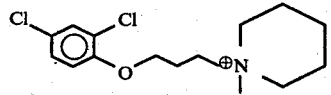 | Br⊖ | |

-continued

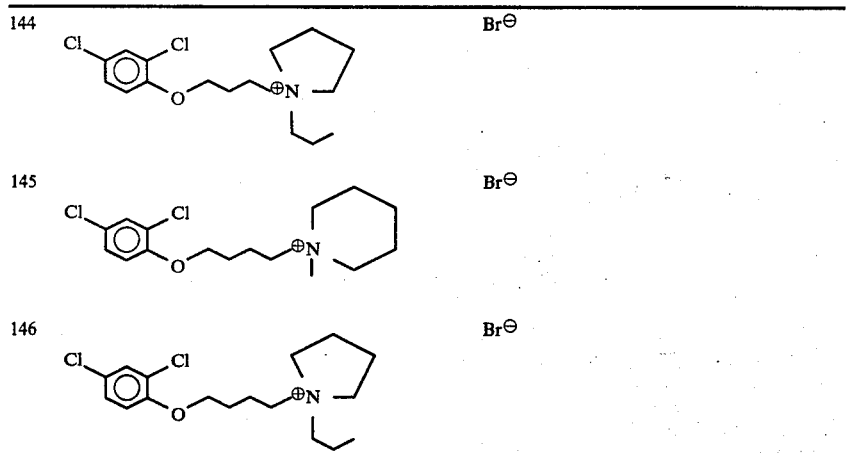

The new active ingredients according to the invention influence plant metabolism, and may therefore be used as plant growth regulators.

Experience has shown that plant growth regulators may have either one or several different effects on plants.

The diversity of action of growth regulators depends especially on (a) the type and variety of plant;

(b) the time applied, with reference to the development stage of the plants and the time of year;

(c) the place and method of application (seed treatment, soil treatment, or application to leaves);

(d) climatic factors (sunshine duration, average temperature, precipitate);

(e) soil conditions (including fertilization);

(f) the formulation of the active ingredient; and (g) the concentration at which the active ingredient is applied.

At all events, plant growth regulators have a positive and desired effect on crop plants.

A description of some of the various possibilities of using the growth regulators according to the invention in agriculture and horticulture is given below.

A. With the compounds according to the invention, vegetative plant growth can be inhibited to a considerable extent, a fact which is manifested particularly in a reduction in plant height. The treated plants thus have a compact habit. The use of the compounds according to the invention also results in an increased chlorophyll content—the leaf color is darker. Consequently, an increased rate of photosynthesis and increased yields may be expected.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

A further mechanism for increasing yields with growth regulators is based on the fact that the nutrients are employed to a greater extent for blossom and fruit formation, whereas vegetative growth is restricted. Because the leaf or plant mass is relatively low, this also counteracts attack by various, particularly fungal, diseases.

The inhibition of vegetative growth also makes closer planting possible in numerous crops, which means an increase in yield based on the area cropped. The compounds according to the invention are particularly suitable for suppressing vegetative growth in crop plants such as soybeans, sunflowers, groundnuts, rape, ornamentals, cotton, rice and grasses.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for readily controllable defoliation of plants.

The action of the compounds according to the invention is superior to that of prior art growth regulators. This action is manifested not only in monocotyledon crops, e.g., cereals such as wheat, barley, rye, oats and rice or Indian corn or grasses, but also particularly in dicotyledons (e.g., sunflowers, tomatoes, groundnuts, grapes, cotton, rape and, particularly, soybeans) and various ornamentals such as chrysanthemums, poinsettias and hibiscus.

The compounds according to the invention may be applied to the crop either by treating the seed, treating the soil, i.e., through the roots, or—the method particularly preferred—by spraying the leaves. Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.001 to 12 kg/ha, preferably from 0.01 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active-ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine, ketones, eg. cyclohexanone, dimethylformamide, and water; solid carriers, for example natural rock powders, e.g. kaolin, alumina, talc and chalk, and synthetic rock powders, e.g. highly disperse silica and silicates; emulsifiers, and other surfactants, for example non-ionic and anionic emulsifiers, e.g. polyoxyethylene fatty alcohol ethers and alkylsulfonates, and dispersants, for example lignin, sulfite waste liquors and methylcellulose. It is preferred to use the compounds according to the invention in aqueous solution, if desired with the addition of water-miscible organic solvents such as methanol or other lower alcohols, acetone, dimethylformamide or N-methylpyrrolidone. The formulations iin general contain from 0.1 to 95% by weight of active ingredient, preferably from 0.5 to 90%.

The formulations, and the ready-to-use preparations obtained therefrom, e.g. solutions, emulsions, suspensions, powders, dusts, pastes or granules, are applied in the conventional manner, e.g. preemergence, postemergence, or as seed disinfectants.

The following are examples of formulations.

I. 20 parts by weight of the compound of Example 10 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of the compound of Example 16 is intimately mixed with 97 parts by weight of particulate kaolin. A dust is obtained containing 3% by weight of the active ingredient.

III. 30 parts by weight of the compound of Example 19 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 21 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt % of active ingredient.

V. 20 parts of the compound of Example 30 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of the compound of Example 28 is mixed with 10 parts by weight of N-methyl-α-pyrrolidone. A mixture is obtained which is suitable for application in the form of very fine drops.

VII. 20 parts by weight of the compound of Example 29 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 31 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IX. 10 parts by weight of the compound of Example 10, 20 parts by weight of polyoxyethylene sorbitan monolaurate (Tween 20 ®), 20 parts by weight of methanol and 50 parts by weight of water are stirred to give a solution containing 10 wt% of the active ingredient. More dilute solutions may be prepared by adding water.

The active ingredients according to the invention may also, in these application forms, be mixed and applied with other active ingredients, e.g., herbicides, insecticides, other growth regulators, fungicides, and fertilizers. Mixture with other growth regulators often broadens the spectrum of action; synergistic effects also occur with a number of these mixtures; i.e., the action of the combination product is greater than that of the individual components added together.

Examples of fungicides which may be combined with the compounds according to the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene-bis (thiocarbamoyl)-disulfide, zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitrophenol derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimido-phosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, D,L-methyl-N-(2,6-dimethylphenyl)-N-fur-2-yl-alaninate, methyl D,L-N-(2,6-dimethylphenyl)-N-(2'-methoxyacetyl)-alaninate, diisopropyl 5-nitroisophthalate, 2,5-dimethyl-furan-3-carboxylic acid anilide, 2,5-dimethylfuran-3-carboxylic acid cyclohexylamide, 2-methyl-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, 2,3-dichloro-1,4-naphthoquinone, 1,4-dichloro-2,5-dimethoxybenzene, p-dimethylaminobenzene diazosodium sulfonate, 1-chloro-2-nitropropane, polychloronitrobenzenes such as pentachloronitrobenzene, methyl isocyanate, fungicidal antibiotics such as griseofulvin or kasugamycin, tetrafluorodichloroacetone, 1-phenyl-thiosemicarbazide, Bordeaux mixture, nickel-containing compounds and sulfur.

The following Examples A and B demonstrate the action of the compounds according to the invention as planth growth regulators; however, further applications as growth regulators are not excluded.

EXAMPLE A; GREENHOUSE EXPERIMENTS

To determine the growth-regulating properties of the compounds, plastic pots 12.5 cm in diameter were filled with a peat culture substrate provided with sufficient nutrients, and test plants were grown therein.

The compounds to be examined were sprayed onto the plants as aqueous formulations. The growth-regulating action observed was confirmed at the end of the experiments by length measurements. These values were then compared with those obtained on untreated plants. Agents used for comparison purposes were

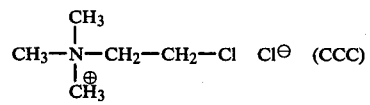

and

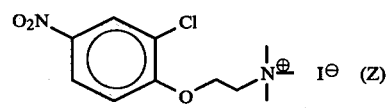

disclosed in German Laid-Open Application DE-OS No. 2,017,497.

Not only was the height of the plants reduced—the leaves also took on a deeper color. The increased chlorophyll content would seem to indicate a higher rate of photosynthesis, thus making for an increased yield.

The individual figures are given in Tables 1 to 4.

EXAMPLE B; VEGETATION EXPERIMENTS

Soybeans of the SRF 400 variety were grown under optimum conditions in a neutral sandy loam, provided with sufficient nutrients, in Mitscherlich vessels in a conditioned chamber. The compounds to be examined were sprayed onto the plants as aqueous formulations, at rates equivalent to 0.5, 1.0 and 1.5 kg of active ingredient per hectare. In each case, 2 vessels formed one experimental variant. The shortening effect observed was confirmed at the end of the experiments by length measurements. Agents used for comparison purposes were

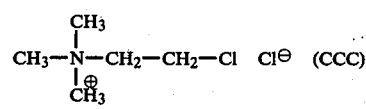

and

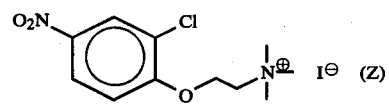

disclosed in German Laid-Open Application DE-OS No. 2,017,497.

The individual figures are given in Table 5.

TABLE 1

| Influence on the height of monocotyledons Lawn, postemergence treatment; duration of expt.: 45 days | | | |
|---|---|---|---|
| Compound | Concentration in mg of a.i./vessel | Growth height cm | % |
| untreated | — | 9.1 | 100 |
| CCC | 6 | 8.5 | 93.4 |
| 10 | 6 | 7.5 | 82.4 |

(a.i. = active ingredient)

TABLE 2.1

Influence on height of dicotyledons; greenhouse experiments
Soybeans, SRF 400 variety
postemergence treatment; duration of expt.: 31 days

| Compound | Concentration in mg of a.i./vessel | Growth height cm | % |
|---|---|---|---|
| untreated | — | 25.3 | 100 |
| CCC | 1.5 | 24.5 | 96.8 |
| | 6.0 | 23.5 | 92.9 |
| 10 | 1.5 | 15.0 | 59.3 |
| | 6.0 | 13.5 | 53.4 |
| 16 | 1.5 | 21.5 | 85.0 |
| | 6.0 | 15.0 | 59.3 |
| 17 | 1.5 | 16.0 | 63.2 |
| | 6.0 | 13.5 | 53.4 |
| 19 | 1.5 | 17.0 | 67.2 |
| | 6.0 | 15.0 | 59.3 |
| 27 | 1.5 | 18.0 | 71.2 |
| | 6.0 | 16.5 | 65.2 |
| 28 | 1.5 | 16.5 | 65.2 |
| | 6.0 | 14.5 | 57.3 |
| 29 | 1.5 | 15.0 | 59.3 |
| | 6.0 | 14.0 | 55.3 |
| 31 | 1.5 | 17.0 | 67.2 |
| | 6.0 | 13.0 | 51.4 |

TABLE 2.2

Influence on the height of dicotyledons; greenhouse experiments
Soybeans, SRF 400 variety
postemergence treatment; duration of expt.: 31 days

| Compound | Concentration in mg of a.i./vessel | Growth height % |
|---|---|---|
| untreated | — | 100 |
| CCC | 1.5 | 92.5 |
| | 6.0 | 83.0 |
| Z | 1.5 | 94.3 |
| | 6.0 | 92.5 |
| 5 | 1.5 | 84.9 |
| | 6.0 | 73.6 |
| 7 | 1.5 | 79.2 |
| | 6.0 | 71.7 |
| 8 | 1.5 | 43.4 |
| | 6.0 | 37.7 |
| 12 | 1.5 | 83.0 |
| | 6.0 | 71.7 |
| 14 | 1.5 | 47.2 |
| | 6.0 | 41.5 |
| 22 | 1.5 | 49.1 |
| | 6.0 | 34.0 |
| 23 | 1.5 | 52.8 |
| | 6.0 | 45.3 |
| 24 | 1.5 | 67.9 |
| | 6.0 | 58.5 |
| 25 | 1.5 | 50.0 |
| | 6.0 | 52.1 |

TABLE 2.4

Influence on the height of dicotyledons; greenhouse experiments
Soybeans, SRF 400 variety
postemergence treatment; duration of expt.: 31 days

| Compound | Concentration in mg of a.i./vessel | Growth height % |
|---|---|---|
| untreated | — | 100 |
| CCC | 1.5 | 85.6 |
| | 6.0 | 85.6 |
| 41 | 1.5 | 48.0 |
| | 6.0 | 41.1 |
| 42 | 1.5 | 41.1 |
| | 6.0 | 37.7 |
| 44 | 1.5 | 54.8 |
| | 6.0 | 41.1 |

TABLE 2.5

Influence on the height of dicotyledons; greenhouse experiments
Soybeans, SRF 400 variety
postemergence treatment; duration of expt.: 31 days

| Compound | Concentration in mg of a.i./vessel | Growth height % |
|---|---|---|
| untreated | — | 100 |
| CCC | 1.5 | 98.0 |
| | 6.0 | 91.4 |
| 33 | 1.5 | 79.7 |
| | 6.0 | 63.1 |
| 38 | 1.5 | 59.8 |
| | 6.0 | 53.2 |
| 43 | 1.5 | 38.2 |
| | 6.0 | 34.9 |
| 54 | 1.5 | 66.5 |
| | 6.0 | 59.8 |
| 58 | 1.5 | 76.4 |
| | 6.0 | 56.5 |
| 60 | 1.5 | 53.2 |
| | 6.0 | 46.5 |
| 82 | 1.5 | 49.8 |
| | 6.0 | 43.2 |
| 85 | 1.5 | 89.7 |
| | 6.0 | 89.7 |
| 102 | 1.5 | 53.2 |
| | 6.0 | 43.2 |
| 108 | 1.5 | 49.8 |
| | 6.0 | 41.5 |

TABLE 2.6

Influence on the height of dicotyledons; greenhouse experiments
Soybeans, SRF 400 variety
postemergence treatment, duration of expt.: 31 days

| Compound | Concentration in mg of a.i./vessel | Growth height % |
|---|---|---|
| untreated | — | 100 |
| CCC | 1.5 | 90.0 |
| | 6.0 | 90.0 |
| 35 | 1.5 | 83.0 |

TABLE 2.7-continued

Influence on the height of dicotyledons; greenhouse experiments
Soybeans, SRF 400 variety
postemergence treatment; duration of expt.: 31 days

| Compound | Concentration in mg of a.i./vessel | Growth height % |
|---|---|---|
|  | 6.0 | 48.8 |
| 15 | 1.5 | 67.1 |
|  | 6.0 | 48.8 |
| 48 | 1.5 | 77.2 |
|  | 6.0 | 77.2 |
| 65 | 1.5 | 81.3 |
|  | 6.0 | 75.2 |
| 101 | 1.5 | 67.1 |
|  | 6.0 | 63.0 |

TABLE 2.8

Influence on the height of dicotyledons; greenhouse experiments
Soybeans, SRF 400 variety
postemergence treatment; duration of expt.: 31 days

| Compound | Concentration in mg of a.i./vessel | Growth height % |
|---|---|---|
| untreated | — | 100 |
| CCC | 1.5 | 90.9 |
|  | 6.0 | 77.9 |
| 39 | 1.5 | 65.0 |
|  | 6.0 | 47.1 |
| 97 | 1.5 | 50.3 |
|  | 6.0 | 40.3 |
| 106 | 1.5 | 69.6 |
|  | 6.0 | 50.3 |
| 107 | 1.5 | 71.4 |
|  | 6.0 | 53.6 |
| 110 | 1.5 | 55.2 |
|  | 6.0 | 52.0 |
| 111 | 1.5 | 61.7 |
|  | 6.0 | 52.0 |
| 112 | 1.5 | 56.8 |
|  | 6.0 | 52.0 |
| 113 | 1.5 | 64.9 |
|  | 6.0 | 53.6 |

TABLE 2.9

Influence on the height of dicotyledons; greenhouse experiments
Soybeans, SRF 400 variety
postemergence treatment; duration of expt.: 31 days

| Compound | Concentration in mg of a.i./vessel | Growth height % |
|---|---|---|
| untreated | — | 100 |
| CCC | 1.5 | 91.3 |
|  | 6.0 | 76.1 |
| 121 | 1.5 | 91.3 |
|  | 6.0 | 76.1 |
| 122 | 1.5 | 87.5 |
|  | 6.0 | 76.1 |
| 123 | 1.5 | 87.5 |
|  | 6.0 | 87.5 |
| 124 | 1.5 | 87.5 |
|  | 6.0 | 83.7 |
| 126 | 1.5 | 72.2 |
|  | 6.0 | 64.6 |
| 134 | 1.5 | 68.4 |
|  | 6.0 | 64.6 |

TABLE 3

Influence on the height of dicotyledons; greenhouse experiments
Spring rape, Cosa variety
Postemergence treatment; duration of expt.: 25 days

| Compound | Concentration in mg of a.i./vessel | Growth height cm | % |
|---|---|---|---|
| untreated | — | 25.5 | 100 |
| CCC | 1.5 | 23.0 | 90.2 |
|  | 6.0 | 21.5 | 84.3 |
| 19 | 1.5 | 20.0 | 78.4 |

TABLE 3-continued

Influence on the height of dicotyledons; greenhouse experiments
Spring rape, Cosa variety
Postemergence treatment; duration of expt.: 25 days

| Compound | Concentration in mg of a.i./vessel | Growth height cm | % |
|---|---|---|---|
|  | 6.0 | 15.0 | 58.8 |
| 27 | 1.5 | 22.5 | 88.2 |
|  | 6.0 | 20.0 | 78.4 |
| 28 | 1.5 | 22.5 | 88.2 |
|  | 6.0 | 17.0 | 66.7 |
| 29 | 1.5 | 22.0 | 86.3 |
|  | 6.0 | 18.0 | 70.6 |
| 31 | 1.5 | 23.0 | 90.2 |
|  | 6.0 | 18.0 | 70.6 |

TABLE 4

Influence on the height of dicotyledons; greenhouse experiments
Sunflowers
Postemergence treatment; duration of expt.: 21 days

| Compound | Concentration in mg of a.i./vessel | Growth height cm | % |
|---|---|---|---|
| untreated | — | 28.5 | 100 |
| CCC | 1.5 | 26.0 | 91.2 |
|  | 6.0 | 24.0 | 84.2 |
| 10 | 1.5 | 25.0 | 87.7 |
|  | 6.0 | 20.0 | 70.2 |
| 16 | 1.5 | 23.0 | 80.7 |
|  | 6.0 | 18.0 | 63.2 |
| 17 | 1.5 | 26.0 | 91.2 |
|  | 6.0 | 20.0 | 70.2 |
| 19 | 1.5 | 22.0 | 77.2 |
|  | 6.0 | 21.0 | 73.7 |
| 27 | 1.5 | 19.0 | 66.7 |
|  | 6.0 | 15.0 | 52.6 |
| 28 | 1.5 | 18.0 | 63.2 |
|  | 6.0 | 15.0 | 52.6 |
| 29 | 1.5 | 18.0 | 63.2 |
|  | 6.0 | 16.0 | 56.1 |
| 31 | 1.5 | 20.0 | 70.2 |
|  | 6.0 | 16.0 | 56.1 |

TABLE 5

Vegetation experiment in conditioned chamber
Soybeans, SRF 400 variety;
Postemergence treatment; duration of expt.: 69 days

| Compound | Concentration in mg of a.i./vessel | Growth height cm | % |
|---|---|---|---|
| untreated | — | 98.8 | 100 |
| CCC | 0.5 | 96.0 | 97.2 |
|  | 1.0 | 94.5 | 95.7 |
|  | 1.5 | 91.0 | 92.1 |
| Z | 0.5 | 97.5 | 98.7 |
|  | 1.0 | 95.0 | 96.2 |
|  | 1.5 | 95.0 | 96.2 |
| 10 | 0.5 | 82.5 | 83.5 |
|  | 1.0 | 76.5 | 77.4 |
|  | 1.5 | 64.0 | 64.8 |
| 29 | 0.5 | 86.5 | 87.6 |
|  | 1.0 | 78.5 | 79.5 |
|  | 1.5 | 73.5 | 74.4 |

We claim:
1. A substituted alkylammonium salt of the formula

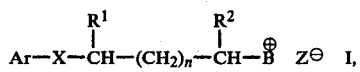

where Ar denotes phenyl substituted by trifluoromethyl or cyano, or by 2 to 3 indentical or different substituents selected from the group consisting of alkyl, alkenyl, alkynyl, cycloalkyl, alkoxy, trifluoromethyl, alkylcarbonylamino, alkylsulfonyl, alkylaminosulfonyl, dialkylaminosulfonyl, all of a maximum of 6 carbon atoms, fluoro, chloro, bromo, iodo, cyano, aminosulfonyl, phenyl and benzyl, X denotes oxygen or sulfur, n denotes one of the integers 0, 1 and 2, $R^1$ and $R^2$ are identical or different and each denotes hydrogen or $C_1$-$C_4$-alkyl, B denotes

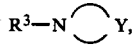

Y denoting a —$(CH_2)_4$—, —$(CH_2)_5$—, —$(CH_2)_7$— group which is unsubstituted or substituted by from 1 to 3 identical or different radicals selected from the group consisting of $C_1$-$C_4$-alkyl, $C_1$-$C_4$-alkoxy, chloro, bromo, hydroxy and cyano, and $R^3$ denoting linear or branched $C_1$-$C_6$-alkyl, $C_2$-$C_6$-alkenyl or $C_2$-$C_6$-alkynyl, each of which is unsubstituted or substituted by halogen, hydroxy, cyano, $C_1$-$C_4$-alkoxy or $C_1$-$C_4$-alkylcarbonyl, and Z denotes the anion of any non-phytotoxic acid HX.

2. A substituted alkyl ammonium salt as set forth in claim 1, wherein X is oxygen, $R^1$ and $R^2$ are both hydrogen, n is zero and $R^3$ is selected from the group consisting of methyl, ethyl, propyl, butyl, allyl, propargyl, 2-chloroethyl, 2-bromoethyl, cyanomethyl, methylcarbonylmethyl, 2-chloropropen-3-yl, 2-methylpropen-3-yl and 2-buten-1-yl.

3. A compound as set forth in claim 1, which is

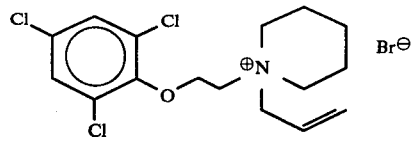

M.p. 155°–156° C.

4. A compound as set forth in claim 1, which is

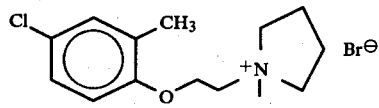

M.p. 58°–61° C.

5. An agent for regulating plant growth, comprising a solid or liquid carrier, and an effective amount of a compound of claim 1.

* * * * *